US012357380B2

(12) United States Patent
DiTomaso

(10) Patent No.: US 12,357,380 B2
(45) Date of Patent: *Jul. 15, 2025

(54) SUCTION CANNULA FOR REMOVAL OF DUCT BLOCKAGE

(71) Applicant: Anthony DiTomaso, Sarasota, FL (US)

(72) Inventor: Anthony DiTomaso, Sarasota, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/517,426

(22) Filed: Nov. 22, 2023

(65) Prior Publication Data

US 2024/0081904 A1   Mar. 14, 2024

Related U.S. Application Data

(63) Continuation of application No. 17/345,048, filed on Jun. 11, 2021, now Pat. No. 11,839,425, which is a continuation of application No. 15/618,115, filed on Jun. 8, 2017, now Pat. No. 11,033,326.

(60) Provisional application No. 62/347,604, filed on Jun. 8, 2016.

(51) Int. Cl.
| | |
|---|---|
| *A61B 18/14* | (2006.01) |
| *A61B 17/00* | (2006.01) |
| *A61B 17/22* | (2006.01) |
| *A61B 17/221* | (2006.01) |
| *A61B 17/30* | (2006.01) |
| *A61B 18/00* | (2006.01) |

(52) U.S. Cl.
CPC ........ *A61B 18/1492* (2013.01); *A61B 17/221* (2013.01); *A61B 2017/00973* (2013.01); *A61B 2017/22079* (2013.01); *A61B 2017/2215* (2013.01); *A61B 2017/306* (2013.01); *A61B 2018/00595* (2013.01); *A61B 2018/00601* (2013.01); *A61B 2217/005* (2013.01)

(58) Field of Classification Search
CPC .............. A61B 17/221; A61B 18/1492; A61B 2017/00973; A61B 2017/22079; A61B 2017/2215; A61B 2017/306; A61B 2018/00595; A61B 2018/00601; A61B 2217/005

See application file for complete search history.

(56) References Cited

U.S. PATENT DOCUMENTS 11,033,326 B2 * 6/2021 DiTomaso ......... A61B 18/1492
11,839,425 B2 * 12/2023 DiTomaso ......... A61B 18/1492

(Continued)

*Primary Examiner* — Mohamed G Gabr
(74) *Attorney, Agent, or Firm* — Jason A. Smith; Shumaker, Loop & Kendrick, LLP

(57) ABSTRACT

Technologies are described for an endoscopic duct clearing system. A cannula can be shaped to pass through an endoscope within an esophagus, into a duodenum, and through an incision in a duodenal papilla. A capture basket may be deployed from a distal end of the cannula. A hand control at the proximate end of the cannula may be operable to position the distal end of the cannula from outside the endoscope into proximity of blockage material. A suction line may be coupled from a suction source to the proximate end of the cannula. A suction control may be coupled to the suction source. The suction control may be operable to adjust a level of suction drawn by the suction source through the distal end of the cannula. The suction control may be adjusted to draw the blockage material against or into the cannula for removal from the patient.

16 Claims, 6 Drawing Sheets

(56) References Cited

U.S. PATENT DOCUMENTS

| | | | |
|---|---|---|---|
| 2004/0049152 A1* | 3/2004 | Nayak | A61B 17/12136 604/509 |
| 2006/0047286 A1* | 3/2006 | West | A61B 17/221 606/114 |
| 2011/0160742 A1* | 6/2011 | Ferrera | A61F 2/82 606/127 |
| 2017/0354405 A1 | 12/2017 | DiTomaso | |
| 2021/0298825 A1 | 9/2021 | DiTomaso | |

* cited by examiner

SUCTION CANNULA FOR REMOVAL OF DUCT BLOCKAGE

CROSS-REFERENCE TO RELATED APPLICATION

This application claims the benefit of U.S. provisional patent application No. 62/347,604, filed on Jun. 8, 2016, entitled "Suction Cannula For Removal of Duct Blockage," which is expressly incorporated herein by reference in its entirety.

BACKGROUND

Blockages, such as gallstones, within the bile ducts can prevent bile from passing into the intestine resulting in various complications such as jaundice. Traditionally, blockages are treated using an endoscopic retrieval procedure where a balloon or other structure is trawled through the common bile duct to mechanically mobilize blockages. There are numerous shortcomings to these traditional approaches. For example, deployment of the balloon or retrieval structure can lose the blockage or even push the blockage deeper into the biliary or pancreatic ducts. Blockages far into the ductal system can be exceedingly difficult to remove. Also, trawling procedures are often complicated by geometries within duct structures, tight angles between duct segments, or awkward positioning of the endoscope within the duodenum. Such complicating geometries can result in blockages slipping past the balloon or retrieval structure. Accordingly there is a need in the art for improved removal of duct blockages in endoscopic clinical procedures.

SUMMARY

Technologies are described for an endoscopic duct clearing system. A cannula can comprise a geometry configured to pass through an endoscope within an esophagus, into a duodenum, and through an incision in a duodenal papilla. A capture basket may be deployed from a distal end of the cannula. A hand control at the proximate end of the cannula may be operable to position the distal end of the cannula from outside the endoscope into proximity of blockage material. A suction line may be coupled from a suction source to the proximate end of the cannula. A suction control may be coupled to the suction source. The suction control may be operable to adjust a level of suction drawn by the suction source through the distal end of the cannula. The suction control may be adjusted to draw the blockage material against or into the cannula for removal from the patient.

It should be appreciated that the above-described subject matter may be implemented as an apparatus, a system, an article of manufacture, or methods/processes associated therewith. These and various other features will be apparent from a reading of the following Detailed Description and a review of the associated drawings.

This Summary is provided to introduce a selection of concepts in a simplified form that are further described below in the Detailed Description. This Summary is not intended to identify key features or essential features of the claimed subject matter, nor is it intended that this Summary be used to limit the scope of the claimed subject matter. Furthermore, the claimed subject matter is not limited to implementations that solve any or all disadvantages noted in any part of this disclosure.

DETAILED DESCRIPTION

Figure 1:
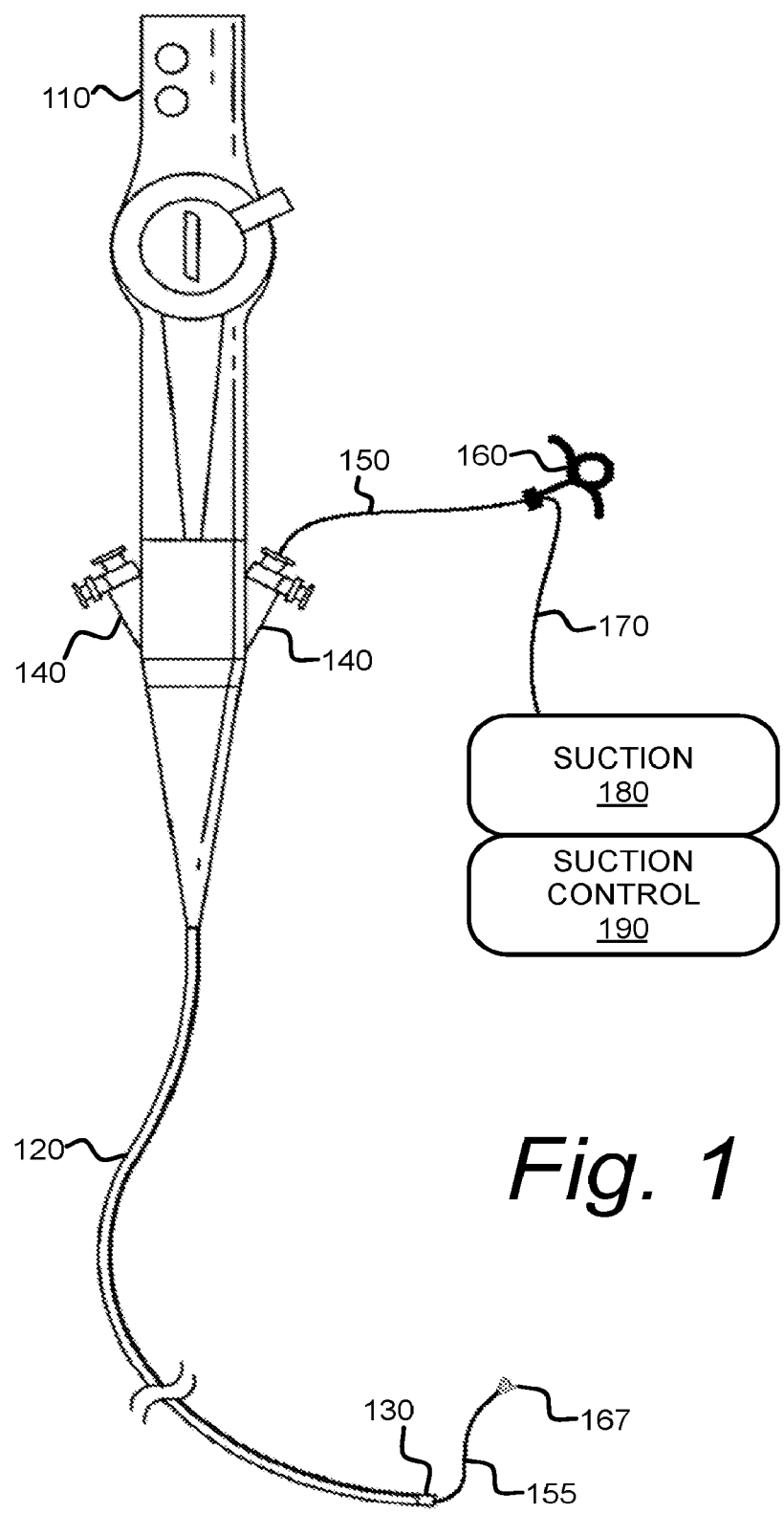
FIG. 1 illustrates an endoscopic suction-cannula system according to one or more embodiments of the technology presented herein.

The following description is directed to technologies for suction-cannula removal of duct blockages in endoscopic clinical procedures. Endoscopic retrograde cholangiopancreatography (ERCP) procedures may be useful to treat blockages of the biliary or pancreatic ductal systems. Through the endoscope, a physician can visualize the inside of the stomach and duodenum. A contrast medium, such as a dye, may be introduced into the ducts in the biliary tree and pancreas for visualization via radiographs. Blockages, such as gallstones, within the bile ducts can prevent bile from passing into the intestine resulting in various complications such as jaundice. Inflammation or infection referred to as cholecystitis may result when the duct that connects the gallbladder to the rest of the biliary tree becomes blocked.

It should be appreciated that the technology presented herein may apply to procedures associated with the various bile ducts, the pancreatic duct, the cystic duct, the hepatic ducts, and/or any other structures associated with the biliary or pancreatic ductal systems.

In the following detailed description, references are made to the accompanying drawings that form a part hereof, and which are shown by way of illustration specific embodiments or examples. Referring now to the drawings, in which like numerals represent like elements through the several figures, aspects of suction-cannula removal of duct blockages will be presented.

FIG. 1 illustrates an endoscopic suction-cannula system according to one or more embodiments of the technology presented herein. An endoscope tube 120 may be operable to insert through the esophagus into the duodenum of a patient. The endoscope body 110 may comprise the external portion of the endoscope, controls, and side ports 140.

A cannula 155 may be inserted into one of the side ports 140, extended through the endoscope tube 120, and emerge from the distal tube tip 130 of the endoscope tube 120. The portion of the cannula 155 remaining outside of the endoscope body 110 may be referred to as the outer cannula 150. The outer cannula 150 may couple to a cannula hand control 160. The cannula hand control 160 may be used to manipulate a capture basket 167 from the distal end of the cannula 155. For example, the capture basket 167 may be extended, retracted, deployed, and/or constricted from the distal end of the cannula 155.

The outer cannula 150 may couple to a suction line 170. The suction line may be coupled to a suction source 180. The suction source 180 may be turned on, turn off, or level adjusted according to a mechanism for suction control 190. The suction control 190 may include a foot pedal to support hands-free operation of the suction source 180 by a clinician employing the endoscope during a procedure. Suction applied to the cannula 155 can draw blockage material into or against the distal end of the cannula 155 and/or the capture basket 167.

The suction line 170 may couple to a filter, bag, vessel, water trap or other container operable to catch waste. This may also protect the suction source 180 from contamination or damage.

Figure 2:
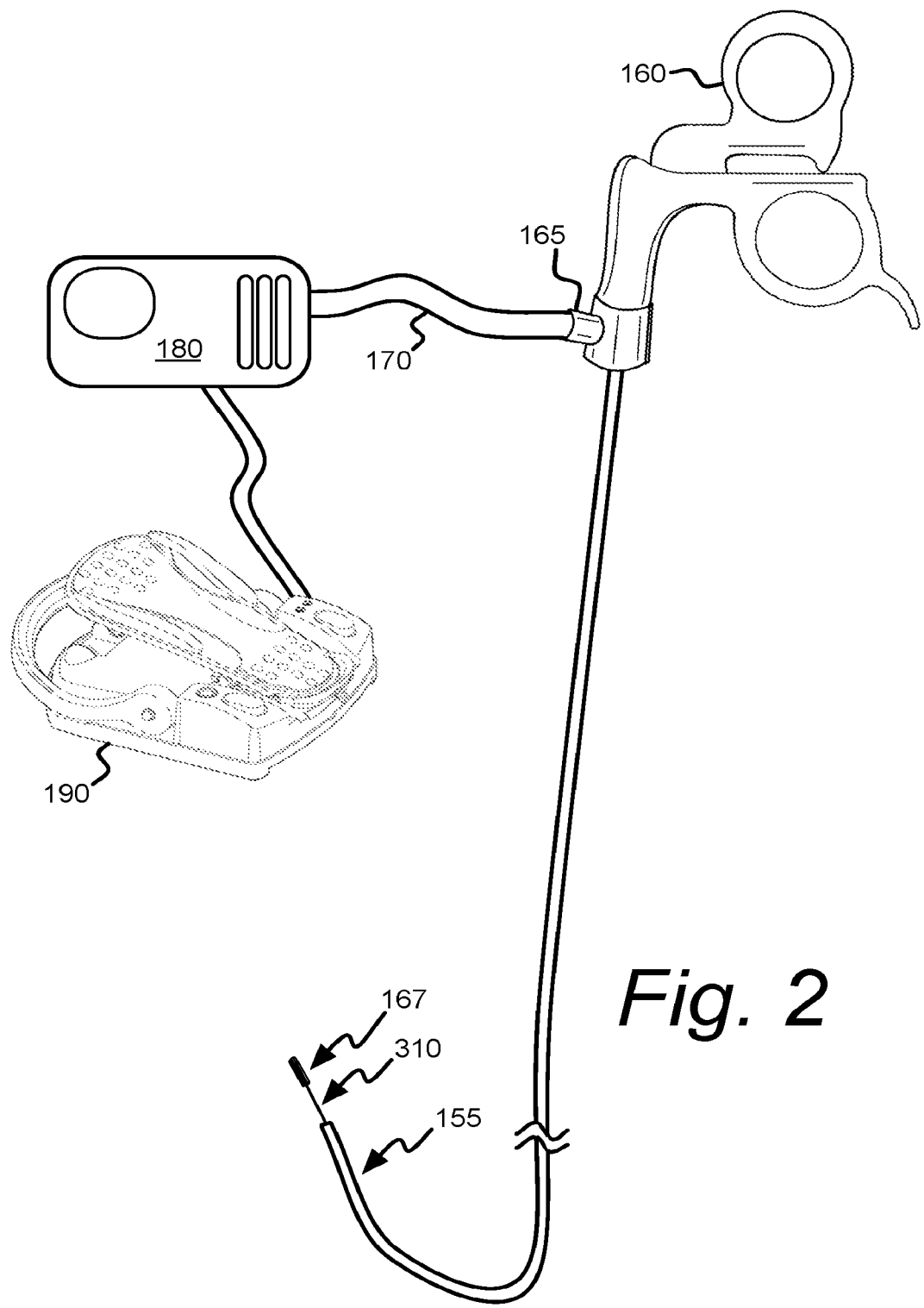
FIG. 2 illustrates an endoscopic suction-cannula system according to one or more embodiments of the technology presented herein.

FIG. 2 illustrates an endoscopic suction-cannula system according to one or more embodiments of the technology presented herein. The cannula 155 may couple to a cannula hand control 160. The cannula hand control 160 may be used to manipulate the capture basket 167 from the distal end of the cannula 155. For example, the capture basket 167 may be extended, retracted, deployed, and/or constricted from the distal end of the cannula 155. Manipulating the cannula hand control 160 can slide a capture stem 310 through cannula 155. The capture stem 310 may extend from the distal end of the cannula 155 where its motion may be used to position and/or deploy the capture basket 167.

The interior space of the cannula 155 may couple to a suction line 170 at a cannula suction port 165. The suction line 170 may be coupled to a suction source 180. The suction source 180 may be turned on, turn off, or level adjusted according to a mechanism for suction control 190 such as a foot pedal.

According to various embodiments, the suction line 170 may be coupled to the suction source 180 where the suction source 180 is controlled by the suction control 190. Alternatively, the suction control 190 may couple directly to, or inline with, the suction line 170 where it can act as a valve or regulator to modulate the effect of the suction from the suction source 180. A debris trap, filter, or other collection mechanism (not illustrated here) may be associated with the suction line 170.

Figure 3:
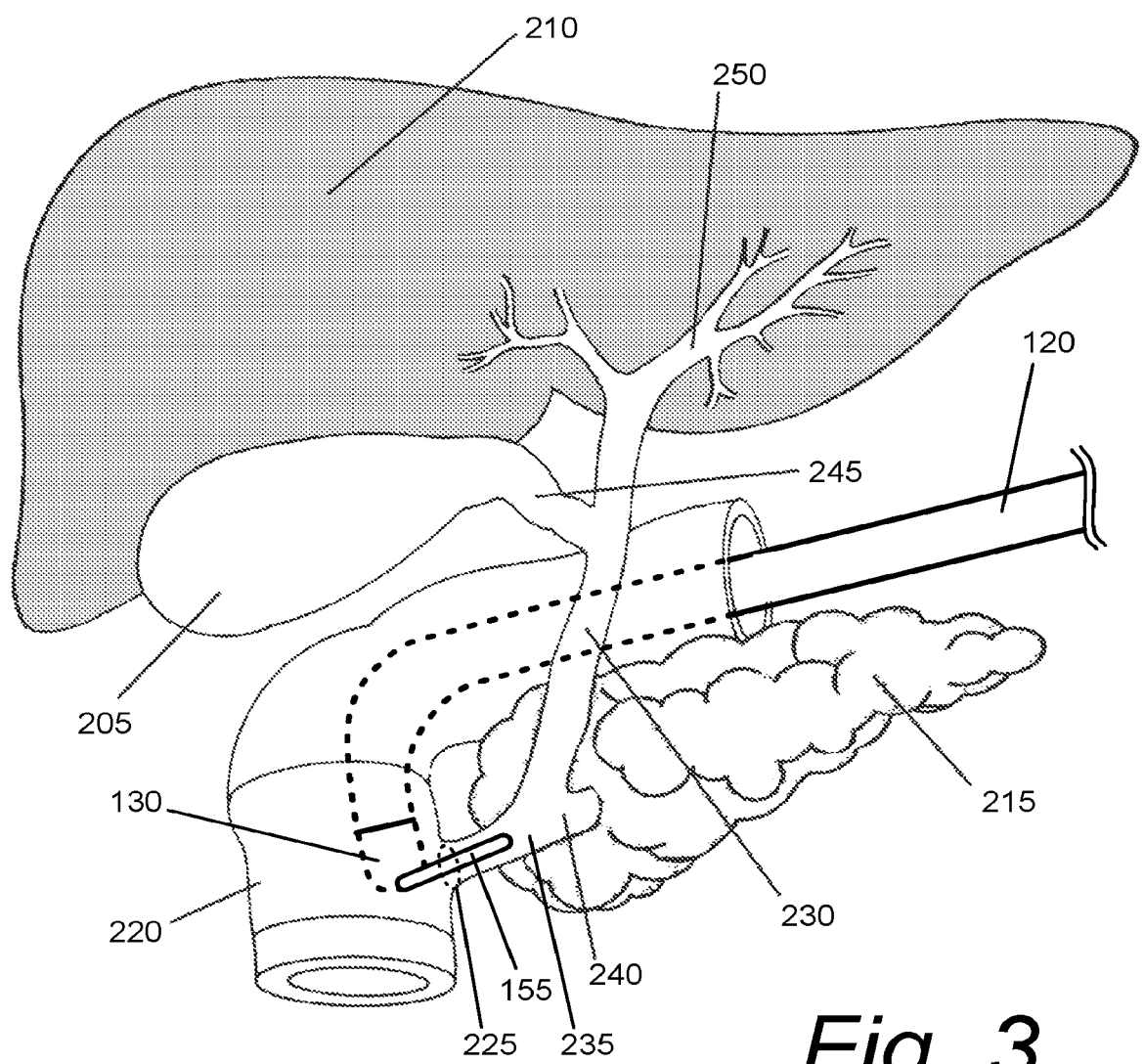
FIG. 3 illustrates the endoscopic suction-cannula system within a physiological application context according to one or more embodiments of the technology presented herein.

FIG. 3 illustrates the endoscopic suction-cannula system within a physiological application context according to one or more embodiments of the technology presented herein. The endoscope tube 120 may be inserted such that the distal tube tip 130 is positioned within the duodenum 220 proximate to the major duodenal papilla 225.

The cannula 155 may be inserted through the major duodenal papilla 225 into the ampulla of Vater 235. From there, the cannula 155 may be manipulated into the common bile duct 230, the pancreatic duct 240, the cystic duct 245, and/or the hepatic duct 250. The pancreatic duct 240 generally couples to the pancreas 215. The cystic duct 245 generally couples to the gallbladder 205. The hepatic duct 250 generally couples to the liver 210. The capture basket 167 may be deployed from the cannula 155 where it is needed for retrieval functions. The cannula 155 may also be used to apply suction for drawing blockage material, such as gallstones 320, from their present location into an area where they may be more readily recovered. The blockage material may also be drawn, dragged, pushed, or flushed out into the duodenum for natural disposal through the lower gastrointestinal system.

Figure 4:
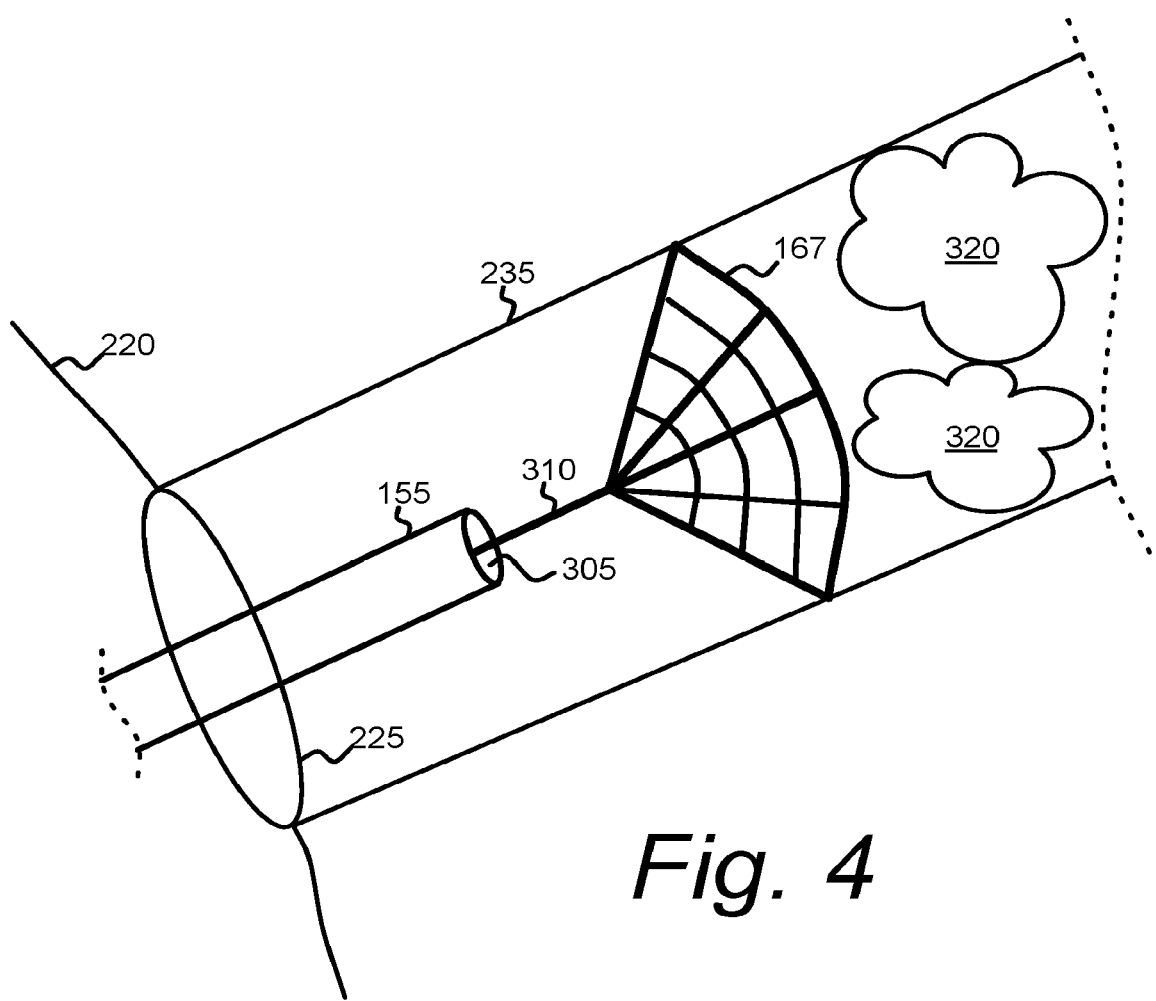
FIG. 4 illustrates a detailed view of the endoscopic suction-cannula system deployed within a duct according to one or more embodiments of the technology presented herein.

FIG. 4 illustrates a detailed view of the endoscopic suction-cannula system deployed within a duct according to one or more embodiments of the technology presented herein. The cannula 155 may be inserted through the major duodenal papilla 225 into the ampulla of Vater 235 from the duodenum 220. A capture stem 310 may extend from the distal end of the cannula 155 through a cannula opening 305. The capture basket 167 may be coupled to the capture stem 310. The capture stem 310 may be mechanically coupled to the cannula hand control 160 to support mechanical manipulation of the capture basket 167.

The suction control 190 can activate the suction source 180 to apply suction to the cannula 155. This suction can generate negative pressure and flow into the cannula opening 305. The pressure and flow can draw blockage material, such as gallstones 320 into the capture basket 167. The pressure and flow may also draw blockage material against the distal end of the cannula 155 at the cannula opening 305. Once captured into the capture basket 167, or against the cannula opening 305, blockage material may be retracted through the endoscope tube 120 for removal.

The cannula 155 may be formed from any flexibly rigid material such as plastics. The cannula 155 may comprise a cross sectional geometry that is substantially circular. The circular geometry may have a diameter of 1-7 mm depending upon various embodiments. The capture stem 310 within the cannula 155 may comprise wire, plastic, or any other rigid yet flexible material.

The capture basket 167 may comprise wire, plastic, nylon, netting, or any other material appropriate for capturing debris from physiological ducts. The capture basket 167 may comprise various example geometries such as the examples presented below. Geometries and structures associated with the capture basket 167 can support the capture basket 167 being modified to conform to the size and/or shape of a duct. Such size/shape conform may be carried out with scraping against, deforming, or injuring the inner surfaces of the duct(s).

It should be appreciated that while the cannula opening 305 and deployed capture basket 167 are illustrated here as being positioned within the ampulla of Vater 235, this intended as merely a non-limiting example. The cannula opening 305 and/or the deployed capture basket 167 may be manipulated throughout the biliary or pancreatic ductal systems. For example, the cannula opening 305 and/or the deployed capture basket 167 may be positioned within, or extended into, and of the ampulla of Vater 235, the common bile duct 230, the pancreatic duct 240, the cystic duct 245, or the hepatic duct 250. The functionally presented herein may be applied in any of these locations within the biliary or pancreatic ductal systems.

Furthermore, the technology presented herein may be widely applied to gallstone removal, pancreatic duct stone removal, polyp retrieval, foreign body removal, stint retrieval, urological stone remove, radiological duct procedures, or any other endoscopic retrieval/recovery process.

Figure 5A:
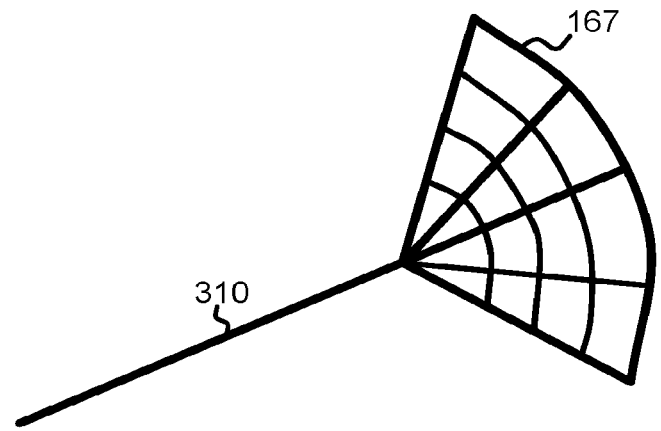
FIG. 5A illustrates a capture basket comprising a substantially cone-shaped geometry according to one or more embodiments of the technology presented herein.
Figure 5B:
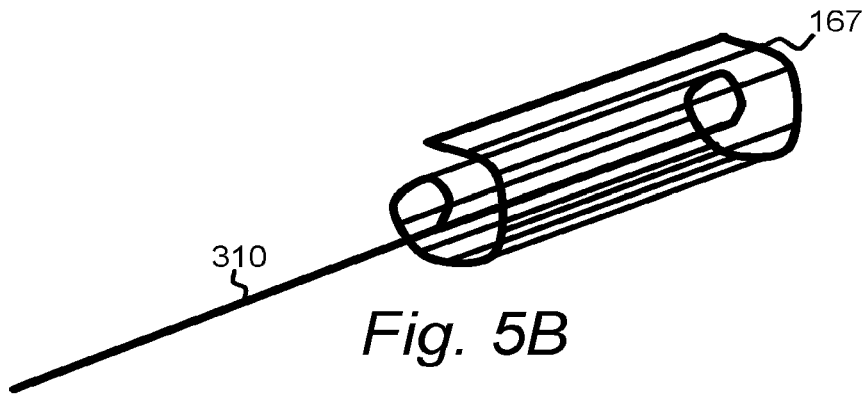
FIG. 5B illustrates a capture basket comprising a substantially rolled-tube-shaped geometry according to one or more embodiments of the technology presented herein.
Figure 5C:
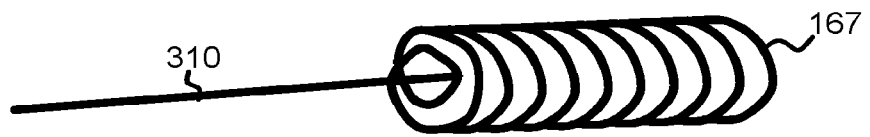
FIG. 5C illustrates a capture basket comprising a substantially coiled or helical geometry according to one or more embodiments of the technology presented herein.

FIG. 5A illustrates a capture basket 167 comprising a substantially cone-shaped geometry according to one or more embodiments of the technology presented herein. FIG. 5B illustrates a capture basket 167 comprising a substantially rolled-tube-shaped geometry according to one or more embodiments of the technology presented herein. FIG. 5C illustrates a capture basket 167 comprising a substantially coiled or helical geometry according to one or more embodiments of the technology presented herein. Various other geometries for the capture basket 167 may be applied without departing from the spirit or scope of the present disclosure.

Figure 6:
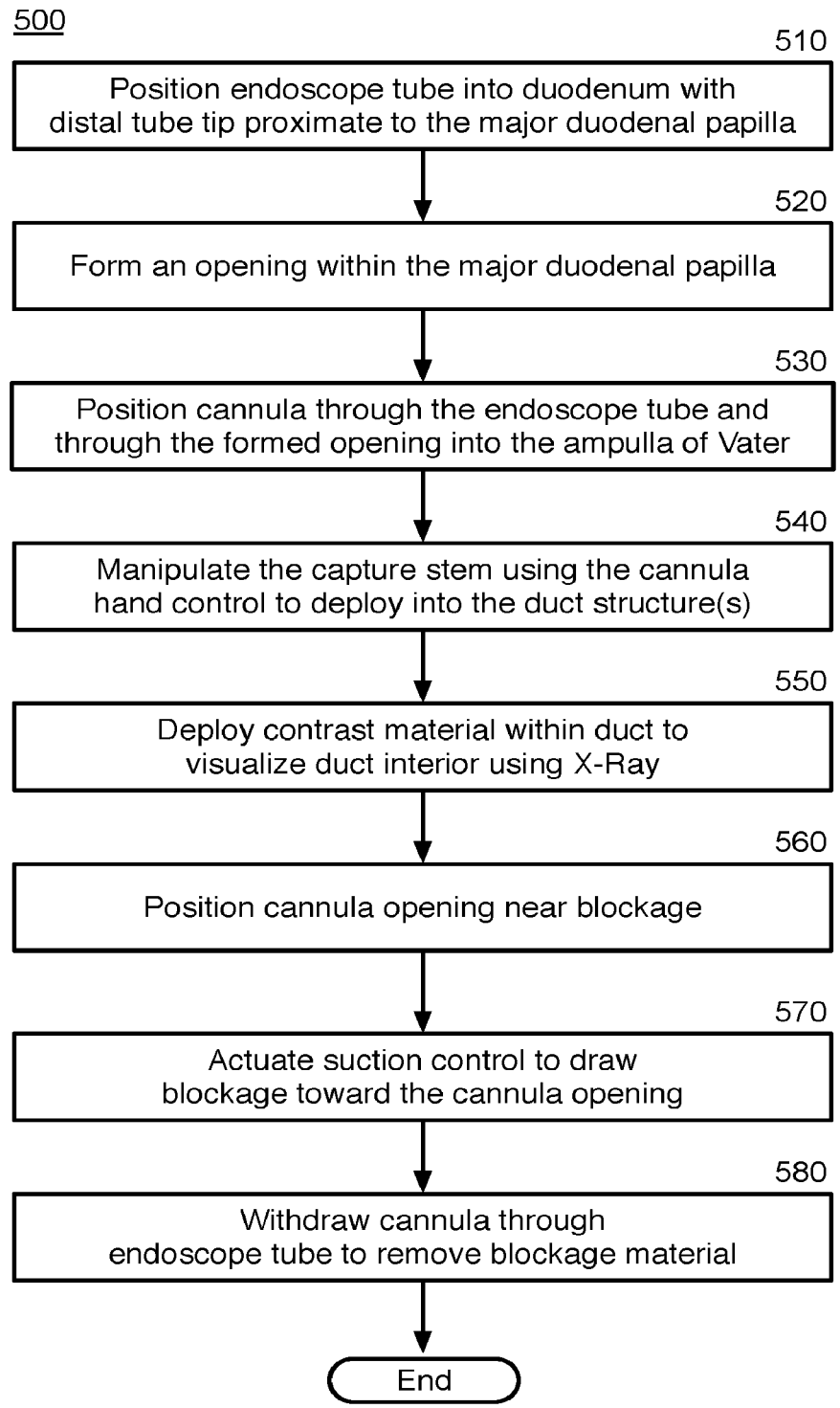
FIG. 6 is a block flow diagram depicting a method for suction-cannula removal of duct blockages associated with endoscopic clinical procedures in accordance with one or more embodiments presented herein. herein.

FIG. 6 is a block flow diagram depicting a method 500 for suction-cannula removal of duct blockages associated with endoscopic clinical procedures in accordance with one or more embodiments presented herein. According to methods and blocks described in the embodiments presented herein, and, in alternative embodiments, certain blocks can be performed in a different order, in parallel with one another, omitted entirely, and/or combined between different example methods, and/or certain additional blocks can be performed, without departing from the scope and spirit of the invention. Accordingly, such alternative embodiments are included in the invention described herein.

In block 510, the endoscope tube 120 may be positioned into the duodenum 220 such that distal tube tip 130 is substantially proximate to the major duodenal papilla 225. This is done optically via fiber or electronic camera associated with the endoscope.

In block 520, an opening may be formed within the major duodenal papilla 225. The opening may be formed using an electrocautery (or thermal cautery) instrument inserted through the endoscope tube 120. Forming of the opening may be referred to as cannulation and may use an instrument such as the CANNULATOME. The opening may be formed adjacent to, starting from, or around, the Sphincter of Oddi within the major duodenal papilla 225. The major duodenal papilla 225 may also be referred to as the papilla of Vater.

In block 530, the cannula 155 may be positioned through the endoscope tube 120 and through the formed opening into the ampulla of Vater 235 and into the bile ducts and/or the pancreatic duct.

In block 540, the capture stem 310 may be manipulated using the cannula hand control 160 to deploy into the biliary or pancreatic ductal systems. It should be appreciated that use of the capture basket 167 may be optional depending upon the particular procedure and circumstances.

In block 550, contrast material, such as a dye, may be deployed within the duct structure to support x-ray imaging, radiographs, fluoroscopy, or other such radiological visualization techniques.

In block 560, the cannula opening 305 may be positioned near the blockage material. Examples of the blockage material may include gallstones 320.

In block 570, the suction control 190 may actuate the suction source 180 to draw the blockage material toward the cannula opening 305. The blockage material may be held by suction against the cannula opening 305 or within the capture basket 167.

In block 580, the cannula 155 may be withdrawn through the endoscope tube 120. The blockage material may be removed through the endoscope tube 120 along with the cannula 155.

Based on the foregoing, it should be appreciated that technologies for suction cannula removal of duct blockages are presented herein. Although the subject matter presented herein has been described in language specific to various example embodiments, it is to be understood that the invention disclosed herein is not necessarily limited to the specific features, materials, dimensions, or structures described herein. Rather, the specific features, materials, dimensions, and structures are disclosed as example forms of implementation. The subject matter described above is provided by way of illustration only and should not be construed as limiting. Various modifications, combinations, and changes may be made to the subject matter described herein without following the example embodiments and applications illustrated and described, and without departing from the true spirit and scope of the present invention, which is set forth in the following claims.

The invention claimed is:

1. An endoscopic duct clearing system comprising:
an endoscope having a first side port configured for receiving a cannula therein;
a cannula having proximal and distal ends with the proximal end arranged outside of the first side port of the endoscope and the distal end of the cannula passed through the endoscope, the distal end of the cannula and the endoscope each configured to be positioned within an esophagus of a patient, into a duodenum of the patient, and through an incision in a duodenal papilla of the patient;
a capture basket that is deployable from the distal end of the cannula, the capture basket having a stem that is connected to the distal end of the cannula, peripheral free edges of an end most portion of the capture basket that are spaced apart from the stem of the capture basket, and a main body positioned directly between the stem and peripheral edges of the end most portion of the capture basket, the capture basket having an open position and a closed position in which the peripheral free edges of the end most portion of the capture basket are substantially aligned with longitudinal axis of the cannula when in a closed position and in which the peripheral free edges of the end most portion of the capture basket diverge from the longitudinal axis of the cannula in an open position;
a hand control coupled to the proximal end of the cannula and configured to manipulate the distal end of the cannula from outside the endoscope, the hand control is spaced apart from the first side port of the endoscope;
a first end of a suction line coupled to the proximal end of the cannula and the hand control via a connection port arranged between the proximal end of the cannula the hand control;
a suction source coupled to a second end of the suction line; and
a suction control coupled to the suction source and operable to adjust a level of suction drawn by the suction source through the distal end of the cannula, wherein
the suction control comprises a foot pedal to support hands-free operation that is coupled to the suction source, and
the capture basket and suction source are configured to actuate blockage material from the patient via the suction source and suction line towards or against the capture basket.

2. The endoscopic duct clearing system of claim 1, wherein the level of suction can draw blockage material into or against the distal end of the cannula for removal from the patient through the endoscope.

3. The endoscopic duct clearing system of claim 1, wherein the suction line is coupled to a filter or container.

4. The endoscopic duct clearing system of claim 1, wherein the capture basket comprises a substantially cylindrical geometry when deployed.

5. The endoscopic duct clearing system of claim 1, wherein the cannula is inserted through a side port of the endoscope.

6. The endoscopic duct clearing system claim 1, wherein the hand control is operable to position the capture basket from the distal end of the cannula.

7. The endoscopic duct clearing system of claim 1, wherein the hand control is operable to deploy and retract the capture basket from the distal end of the cannula.

8. The endoscopic duct clearing system of claim 1, wherein the capture basket comprises a substantially conical geometry when in the open position in which the peripheral free edges of the end most portion of the capture basket radially extends outwardly from the cannula and are angled relative to the longitudinal axis of the cannula such that portions of the peripheral free edges of the end most portion of the capture basket diverge from one another.

9. A method for endoscopic duct clearing, comprising:
   providing an endoscopic duct clearing system according to claim 1;
   positioning an endoscope tube into a duodenum of a patient such that a distal tube tip is proximate to a major duodenal papilla of the patient;
   forming an opening within the major duodenal papilla through the endoscope tube; positioning a distal end of a cannula through the endoscope tube and through the formed opening;
   deploying a capture stem at the distal end of the cannula using a cannula hand control;
   positioning the capture stem proximate to blockage material;
   actuating a suction control to draw the blockage material toward the distal end of the cannula; and
   withdrawing the cannula and the blockage material out of the patient through the endoscope tube.

10. The method for endoscopic duct clearing of claim 9, wherein the blockage material comprises gallstones.

11. The method for endoscopic duct clearing of claim 9, wherein forming an opening within the major duodenal papilla comprises deploying an electrocautery device.

12. The method for endoscopic duct clearing of claim 9, further comprising deploying a contrast material.

13. The method for endoscopic duct clearing of claim 9, wherein actuating the suction control comprises holding the blockage material into or against the distal end of the cannula.

14. The method for endoscopic duct clearing of claim 9, wherein actuating the suction control comprises holding the blockage material into or against the capture basket.

15. The method for endoscopic duct clearing of claim 14, wherein the capture basket comprising a substantial conical geometry when deployed.

16. The method for endoscopic duct clearing of claim 14, wherein the a capture basket comprising a substantial cylindrical geometry when deployed.

* * * * *